United States Patent [19]

Ishiguro

[11] Patent Number: 5,682,895
[45] Date of Patent: Nov. 4, 1997

[54] THREE-DIMENSIONAL ULTRASOUND IMAGE PROCESSING SYSTEM

[75] Inventor: Masaaki Ishiguro, Omiya, Japan

[73] Assignee: Fuji Photo Optical Co., Ltd., Omiya, Japan

[21] Appl. No.: 729,286

[22] Filed: Oct. 10, 1996

[30] Foreign Application Priority Data

Oct. 12, 1995 [JP] Japan .................................. 7-289187

[51] Int. Cl.$^6$ .................................................. A61B 8/00
[52] U.S. Cl. .......................... 128/660.04; 128/660.07; 128/916; 73/620
[58] Field of Search ............................ 128/653.1, 660.04, 128/660.07, 660.08, 660.01, 916; 73/620, 625, 626; 348/44, 45, 51; 395/119, 124, 128

[56] References Cited

U.S. PATENT DOCUMENTS

| | | | |
|---|---|---|---|
| 4,809,065 | 2/1989 | Harris et al. | 348/51 |
| 5,261,404 | 11/1993 | Mick et al. | 128/653.1 |
| 5,533,401 | 7/1996 | Gilmore | 73/622 |

*Primary Examiner*—George Manuel
*Attorney, Agent, or Firm*—Oblon, Spivak, McClelland, Maier & Neustadt, P.C.

[57] ABSTRACT

A 3D ultrasound image processing system which realizes display of 3D ultrasound images on a viewing screen by the use of simple and inexpensive means, the 3D ultrasound images having a cut-out section opened in an region of particular interest to expose to view an internal organ or interior tissue structures in a three-dimensional perspective view. The 3D ultrasound image processing system includes: a two-dimensional ultrasound image capture means for capturing a series of two-dimensional tomographic ultrasound images in sequentially shifted scan positions in a direction perpendicular to planes of the two-dimensional ultrasound images; and a 3D processor including a 3D image generator for compiling picture signals of the sequentially captured two-dimensional ultrasound images directly into picture data of a series of unit picture images lined up in three-dimensionally correlated positions, a 3D image processor for producing an original 3D ultrasound image for display on a viewing screen in relation with a predetermined three-dimensional coordinate system on the basis of picture data of the unit picture images, and a 3D image view processor for opening a cut-out section in part of the original 3D ultrasound image.

6 Claims, 9 Drawing Sheets

FIG. 10a    FIG. 10b    FIG. 10c
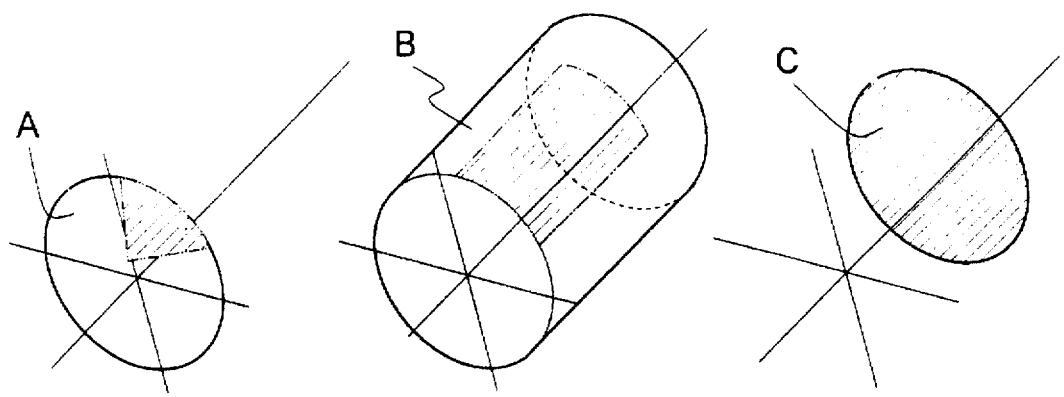
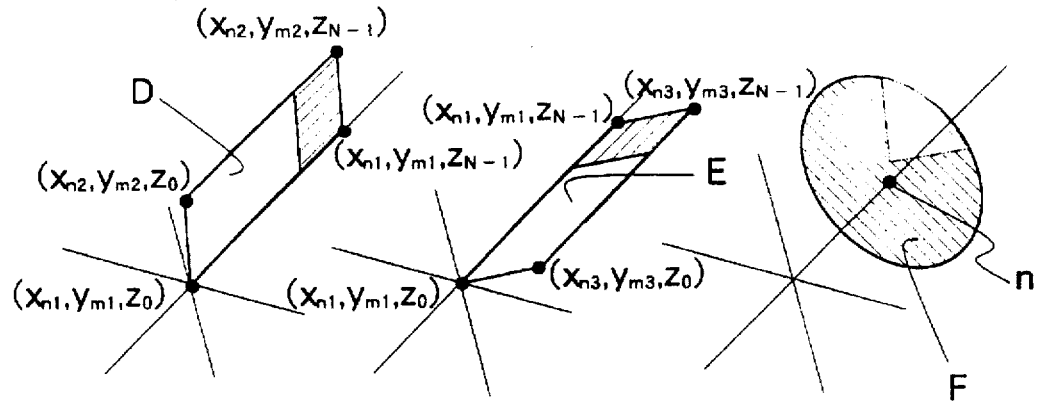
FIG. 10d    FIG. 10e    FIG. 10f
FIG. 12
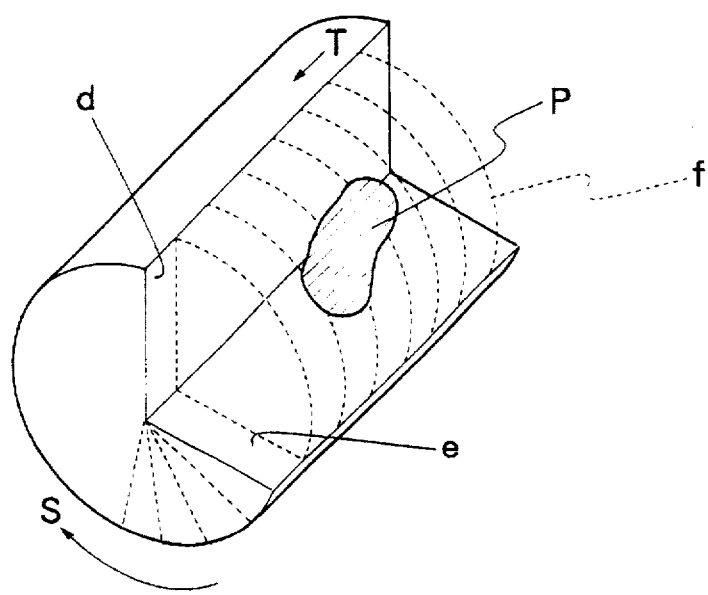

THREE-DIMENSIONAL ULTRASOUND IMAGE PROCESSING SYSTEM

BACKGROUND OF THE INVENTION

1. Field of the Art

This invention relates to three-dimensional (hereinafter abbreviated as "3D" for brevity) ultrasound image processing, and more particularly to a 3D ultrasound image processing system for generating and displaying a 3D ultrasound image of internal tissues or organs on the basis of a series of sequentially captured two-dimensional tomographic ultrasound images and in a cut-out mode in which part of a 3D ultrasound image is hollowed out to expose to view an interior region or regions of particular interest.

2. Prior Art

In ultrasound examination, ultrasound signals are transmitted into patient body through an ultrasound transducer, while receiving return echo signals from body tissues at different depths in the direction of signal transmission, and the return echo signals are processed into video signals to display ultrasound images on a monitor screen. A two-dimensional tomographic ultrasound image is obtained by an ultrasound scan over a predetermined range, that is to say, a B-mode ultrasound image of a predetermined plane section. A large number of two-dimensional ultrasound images of different plane sections, which are captured successively by shifting the scan position in a certain pitch in a predetermined direction, can be converted into a 3D image through image processing operations. Needless to say, as compared with two-dimensional ultrasound images, 3D ultrasound images displayed on a viewing screen are more helpful in clearly grasping the internal tissue structures of scanned regions, and contribute to enhance the accuracy of ultrasound examinations.

A series of two-dimensional ultrasound images, which are each expressed on a two-dimensional X-Y coordinate system, come to have expressions of spatial expanse when lined up along Z-axis of a three-dimensional X-Y-Z coordinate system. In ultrasound images, echoes from internal tissue structures are converted into different light intensities and expressed as variations in luminance on a viewing screen. Therefore, internal tissue structures can be displayed as a 3D image by implementing picture data between adjacent two-dimensional ultrasound images, through linear interpolation based on luminance levels of picture signals in preceding and succeeding two-dimensional ultrasound images. Further, internal tissue structures can be displayed as 3D ultrasound images by dissolving a three-dimensional space on a 3D coordinate system into voxels which contain the luminance information in the entire three-dimensional space scanned. Images of an organ or internal tissue structures of particular interest can be extracted and displayed by image processing based on three-dimensional picture signals.

Any way, in either type of the above-mentioned 3D picture images, a confined three-dimensional space is set up in a particular intracorporeal region of interest by way of the scan range of two-dimensional ultrasound picture images and the direction of alignment of the ultrasound picture images, for the purpose of displaying internal tissue structures or an internal organ in that space in a three-dimensional perspective view. In order to acquire picture data for the 3D images of this sort, it is necessary to produce all the luminance information throughout that 3D space, namely, to create correlated picture data for and between N-number of two-dimensional ultrasound images captured throughout that space. Therefore, 3D ultrasound image processing normally involves a vast amount of picture data and involves extremely complicate data processing operations which take time even by a large-scale data processor.

SUMMARY OF THE INVENTION

In view of the foregoing situations, it is a primary object of the present invention to provide a 3D ultrasound image processing system which can produce and display a 3D ultrasound image on a viewing screen on the basis of sequentially captured two-dimensional ultrasound images, by the use of simple and inexpensive means and in a three-dimensional perspective view with an open cut section which exposes to view an internal organ or interior tissue structures in a scanned intracorporeal region.

In accordance with the present invention, the above-stated objective is achieved by the provision of a 3D ultrasound image processing system which essentially includes a two-dimensional ultrasound image capture means for capturing a series of two-dimensional tomographic ultrasound images in sequentially shifted positions in a direction perpendicular to planes of the two-dimensional ultrasound images, and a 3D processor including a 3D image generator for compiling picture signals of the sequentially captured two-dimensional ultrasound images directly into picture data of a series of unit picture images lined up in three-dimensionally correlated positions, a 3D image processor for producing, on the basis of the unit picture images, an original 3D ultrasound image for display on a viewing screen in relation with a predetermined three-dimensional coordinate system, and a 3D image view processor for opening a cut-out section in part of the original 3D ultrasound image on display on the viewing screen to expose to view interior portions of the 3D ultrasound image on and along cut surfaces of the open cut-out section.

In accordance with the present invention, in order to permit clear three-dimensional grasping of ultrasound images of a scanned subject, its 3D ultrasound image is displayed on a monitor screen in relation with a three-dimensional coordinate system and basically shown in the form of a surface image of a scanned range instead of a see-through image. This 3D image is displayed as an original 3D ultrasound image, which is further processed to expose to view an internal organ or internal tissue structures in a particular region of interest in the scanned range. Namely, by an image cutting process, part of the original 3D ultrasound image on display on a viewing screen is hollowed out by forming an open cut-out section in such a manner as to expose an internal organ or interior tissue structures of interest in a three-dimensionally visible state on and along cut surfaces of the open cut-out section.

In opening a cut-out section on the original 3D ultrasound image on display on a monitor screen, one can select a suitable cut mode and, if necessary, can alter a selected cut mode by changing positions, directions and ranges of cut surfaces in such a way as to permit three-dimensional grasping of a particular internal organ or tissue structures within a scanned range. Upon changing the cut mode for a cut-out section, image re-processing operations are executed solely with regard to altered cut surfaces to simplify signal processing operations and to ensure quick on-screen response to alterations made to cut surfaces of a cut-out section.

BRIEF DESCRIPTION OF THE DRAWINGS

The above and other objects, features and advantages of the invention will become apparent from the following description, taken in conjunction with the accompanying drawings which show by way of example preferred embodiments of the invention and in which:

FIG. 10 is a diagrammatic illustration of elemental picture images constituting surfaces of a 3D ultrasound image including cut surfaces of an open cut-out section;

FIG. 12 is a diagrammatic illustration explanatory of procedures for continuously shifting a cut surface position in an open-cut section.

DESCRIPTION OF PREFERRED EMBODIMENTS

Figure 1:
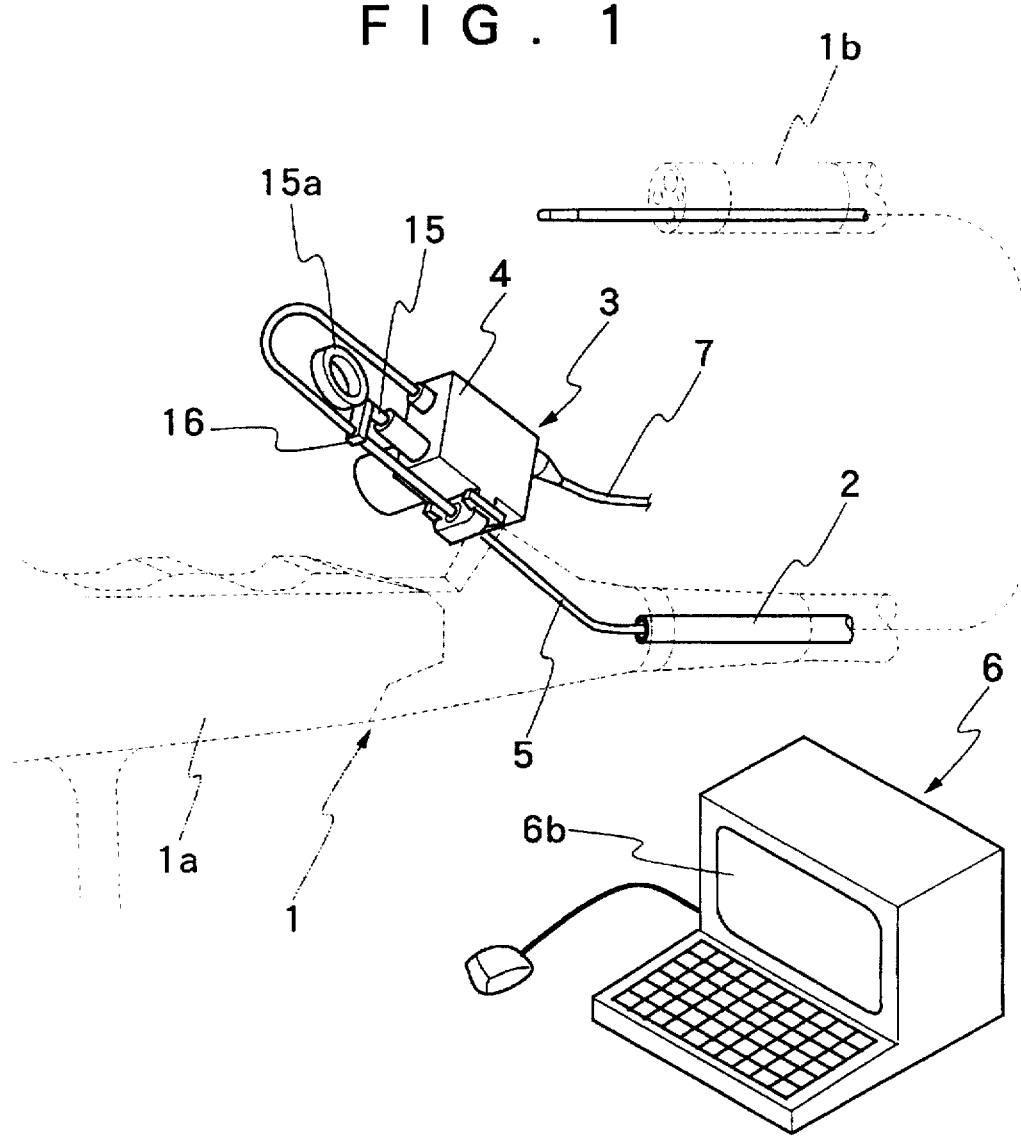
FIG. 1 is a schematic view of a two-dimensional ultrasound image capture system with an endoscopically inserting ultrasound probe.
Figure 2:
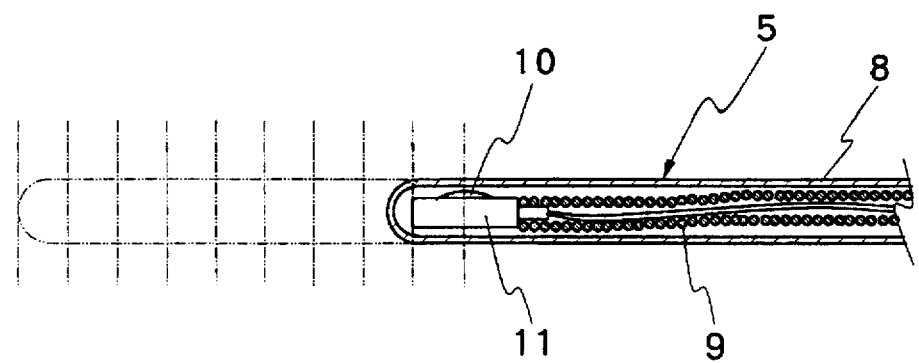
FIG. 2 is a schematic view of a distal end portion of a catheter member of the ultrasound probe.
Figure 3:
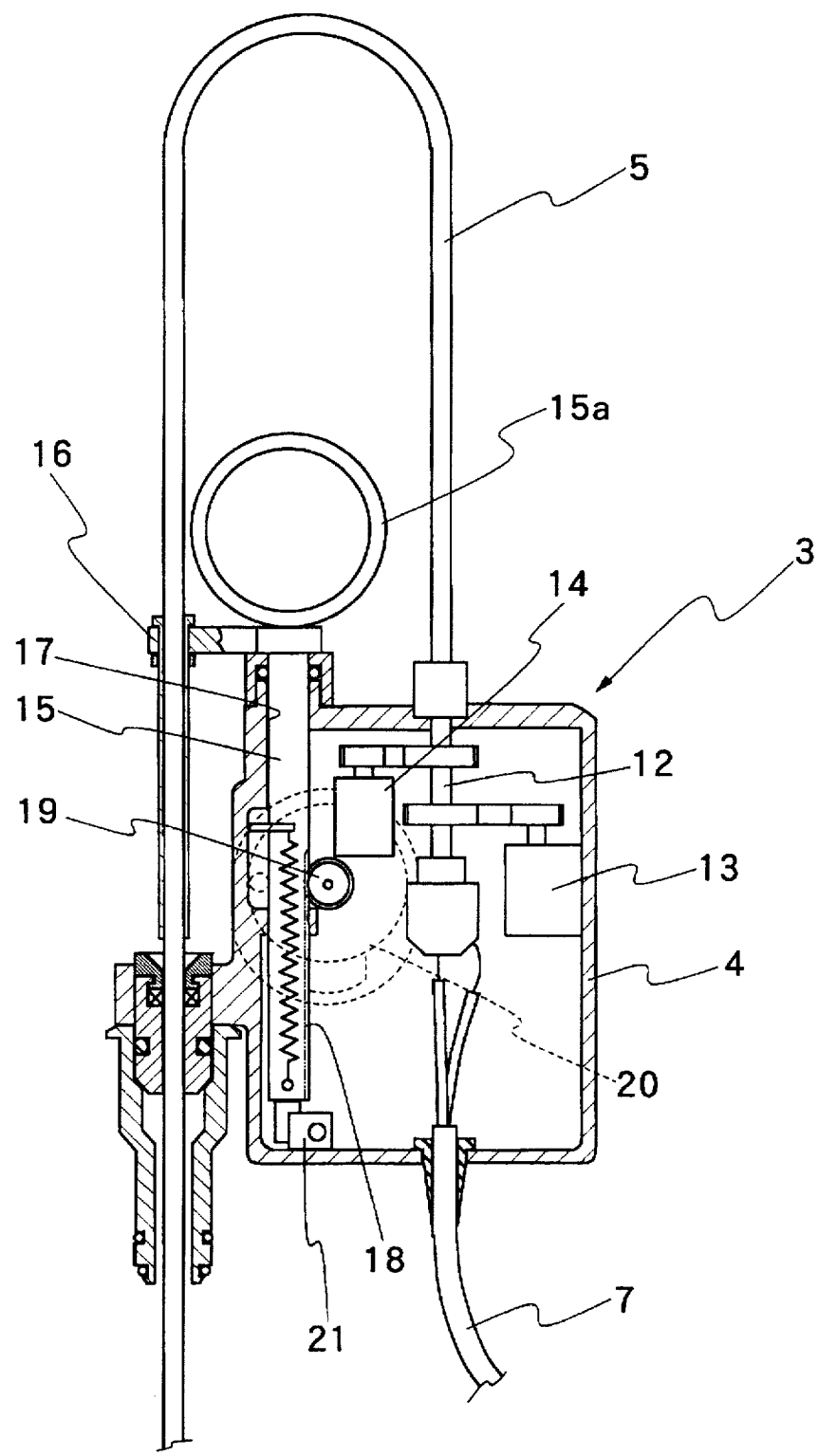
FIG. 3 is a schematic sectional view of a manipulating control head of the ultrasound probe.

Hereafter, the invention is described more particularly by way of its preferred embodiments with reference to the accompanying drawings. FIGS. 1 to 3 shows, as one example of two-dimensional ultrasound image capture means, an ultrasound examination system employing an endoscopically inserting ultrasound probe.

In FIG. 1, indicated at 1 is an endoscope which is largely constituted by a manipulating or gripping head 1a and an elongated insertion rod 1b extended out from the gripping head 1a for insertion into patient body. Extended through the endoscope 1, from a fore end portion of the gripping head 1a to the distal end of the insertion rod 1b, is a biopsy channel 2 for insertion of forceps or other bioptic instruments. For this purpose, the biopsy channel 2 is opened to the outside at the distal end of the insertion rod 1b. Indicated at 3 is an ultrasound probe which is mounted on the gripping head 1a of the endoscope 1, the ultrasound probe 3 having a manipulating head assembly 4 and an elongated catheter member 5 to be introduced into an intracavitary portion of interest through the biopsy channel 2 of the endoscope 1. Led out on the rear side of the manipulating head assembly 4 is a connector cable 7 to be disconnectibly connected to an ultrasound image observation terminal 6 with a monitor screen 6b.

As shown in FIGS. 2 and 3, the catheter member 5 has its component parts enshrouded in a flexible tube 8 which is closed at the fore end. Namely, fitted in the flexible tube 8 is a flexible shaft 9 which consists of tightly wound coils and connected at its fore end to a support base 11 for a single-element ultrasound transducer 10 to transmit rotation thereto. In order to capture sequential ultrasound images, while pushing back and forth the catheter member 5 as a whole, the flexible shaft 9 is turned about its axis within the flexible tube 8 to rotate the ultrasound transducer 10 together with the support base 11.

To this end, the rear or proximal end of the flexible shaft 9 is coupled with a rotational shaft 12 which is mounted within a manipulating head casing and coupled with a motor 13 and encoder 14 by way of pulleys and transmission belts or other coupling means. Accordingly, upon actuating the motor 13, its rotation is transmitted to the flexible shaft 9 through the rotational shaft 12. The rotational angle of the shaft 12 is detected by the encoder 14.

Further, an operating rod 15 which is provided on the manipulating head 4 is connected to a clamp member 16 to grip a proximal end portion of the catheter member 5 which is looped between an entrance opening at the proximal end of the biopsy channel 2 and the manipulating head assembly 4. The operating rod 15 is axially movable into and out of the casing of the manipulating head assembly 4 along a guide 17 to move the catheter member 5 in the linear or axial direction. Normally, the operating rod 15 is retained in an outer position projected outward of the manipulating head 4.

A rack 18 is provided on the operating rod 15 in meshed engagement with a pinion 19 which is connected to an encoder 20 for detection of linear or axial position of the ultrasound transducer 10 at the distal end of the catheter member 5. The operating rod 15 is provided with a finger holder ring 15a in which the operator can put his or her finger at the time of pushing or pulling the operating rod 15 into and out of the manipulating head assembly 4 for axial displacement of the catheter member 5. In FIG. 3, indicated at 21 is a sensor which is located at a predetermined inward stroke end position of the operating rod 15 to detect a reference position of the ultrasound transducer 10 in the linear direction.

With the ultrasound probe 3 arranged as described above, the ultrasound transducer 10 is put in rotation to make radial scans, driven from the motor 13. Signals of a two-dimensional radial ultrasound image are obtained by a radial scan with the ultrasound transducer 10. If the axial position of the ultrasound transducer 10 at the distal end of the catheter member 5 is shifted little by little in an axial direction in a radial scan operation by pulling the operating rod 15 inward or outward, a series of a large number (N-number) of two-dimensional radial ultrasound images can be sequentially obtained in a predetermined pitch in the axial direction. As signals of unit picture images, signals of these N-number of two-dimensional radial ultrasound images are sequentially fed to and processed at a signal processor 6a on the ultrasound image observation terminal 6 to display on the monitor screen 6b a 3D ultrasound image on a three-dimensional coordinate system having the three axes disposed at the angle of 60 degrees with each other to show the 3D image in a regular perspective view.

Figure 4:
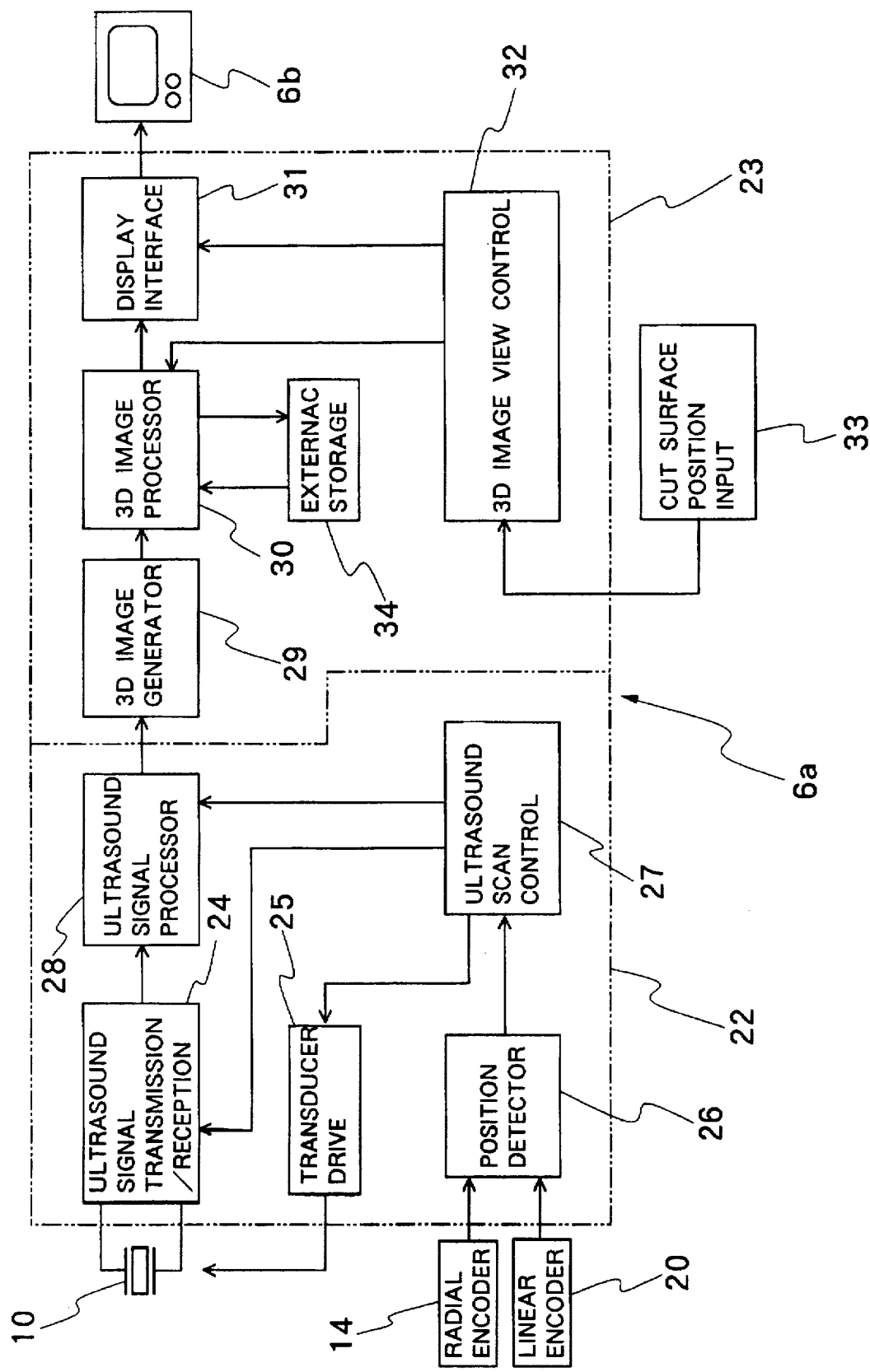
FIG. 4 is a block diagram of an ultrasound signal processor including two- and three-dimensional processors.

FIG. 4 shows the circuit arrangements of the signal processor 6a on the ultrasound image observation terminal 6 which is connected to the ultrasound probe 3 as described above. The signal processor 6a is largely constituted by a two-dimensional ultrasound signal processor 22 and a three-dimensional ultrasound signal processor 23.

The two-dimensional ultrasound signal processor 22 includes an ultrasound signal transmission/reception control circuit 24, a transducer drive circuit 25, a position detection circuit 26, an ultrasound scan control circuit 27, and an ultrasound signal processing circuit 28.

The ultrasound signal transmission/reception control circuit 24, which controls ultrasound signal transmission and reception by the transducer 10, is alternately switched into a signal transmission mode and a signal reception mode. In the signal transmission mode, according to trigger signals which are applied to the ultrasound transducer 10, ultrasound pulse signals are transmitted from the transducer 10 into an intracorporeal region of interest. After signal transmission for a predetermined time duration, the transmission/reception circuit 24 is switched into the signal reception mode to receive return echoes of the transmitted ultrasound pulse signals from various internal tissues of different acoustic impedances existing at different depths of a scanned sectional plane. Return echo signals received by the transducer 10 are converted into electric signals and transferred to the signal transmission/reception circuit 24.

The transducer drive circuit 25 controls the operation of the motor 13 which drives the ultrasound transducer 10, including on-off control on the motor 13 and control of its rotational speed to a predetermined constant level. The position detection circuit 26 detects the transducer position in the rotational direction, that is to say, the angular position of the ultrasound transducer 10 as well as its position in the axial direction. Therefore, the position detection circuit 26 determines the positions of the ultrasound transducer 10 on the basis of signals which are received from rotational angle detection encoder 14 and linear position detection encoder 20 and sensor 21.

The ultrasound scan control circuit 27 controls the ultrasound signal transmission/reception circuit 24 to generate trigger signals during the periods of signal transmission mode, on the basis of angular position signals from the position detection circuit 26. Further, in transferring received ultrasound echo signals successively from the signal transmission/reception circuit 24 to the ultrasound signal processor circuit 28 to capture a series of a large number of two-dimensional radial ultrasound images of linearly shifted positions, the axial position and the angular position in the rotational direction of the ultrasound transducer 10 need to be detected in relation with each acoustic line of the received echo signals. For this purpose, the linear and angular transducer position signals, detected by the position detection circuit 26 by way of the linear and angular position encoders 20 and 14, are also fed to the ultrasound signal processing circuit 28 as linear and axial position data along with the ultrasound echo signals from the signal transmission/reception circuit 24.

Besides, in radial ultrasound scanning operations, it is necessary to detect either an absolute position of the ultrasound transducer 10 or an initial position of a radial scan. In this regard, from the standpoint of simplification of construction, the rotational angle detection encoder 14 is preferred to be an incremental encoder rather than an absolute encoder. This is because, even in the case of an incremental encoder, it is possible to provide an initial scan position indicator and to produce an initial scan position signal in addition to angular position signals of the ultrasound transducer 10. Accordingly, the position detection circuit 26 which is connected to the ultrasound signal processor circuit 28 is supplied with initial scan position signals and angular position signals from the encoder 14, linear reference position signals from the sensor 21, and linear position signals from the encoder 20.

At the ultrasound signal processor circuit 28, two-dimensional ultrasound images are successively generated on the basis of ultrasound echo signals from the signal transmission/reception circuit 24 and initial scan position signals and angular position signals from the position detection circuit 26. In an actual operation for capturing two-dimensional radial ultrasound images, a radial scan is started from the above-mentioned linear reference position in the axial direction, which is detected by the sensor 21 when the operating rod 15 is pushed in, and at the same time from the initial scan position in the radial direction, gating in return echo signals through a predetermined angle and thereafter repeating the radial scan in sequentially shifted positions in the linear direction according to an outward stroke of the operating rod 15. Thus, in total, N-number of two-dimensional radial ultrasound images are successively captured until the operating rod 15 reaches an outer dead end of its stroke range.

In this instance, the ultrasound signal processor circuit 28 basically includes A/D converter and digital scan converter with a framing memory or the like. Video signals of two-dimensional radial ultrasound picture images, which are generated by the ultrasound signal processor 28, are transferred frame by frame from the digital scan converter to the 3D signal processor 23. Picture signals of two-dimensional radial ultrasound picture images to be produced at the output of the ultrasound signal processor circuit 28 should be limited to a particular effective range by confining the capturing of video signals by the framing memory to that effective range instead of capturing all of signals in the entire intracorporeal range which is actually reached by ultrasound signals. By so doing, all of the sequentially captured two-dimensional radial ultrasound images can be trimmed to the same range.

Thus, from the two-dimensional ultrasound signal processor 22 of the above arrangements, the 3D signal processor 23 is successively supplied with video signals of a series of N-number of unit picture images in scan positions which are sequentially shifted in a predetermined pitch in the linear direction. At the 3D processor 23, 3D ultrasound image signals are generated on the basis of the signals of the 1st to N-th unit picture images.

The 3D processor 23 includes a 3D image generator 29, a 3D image processor 30, a display interface 31, a 3D image view control 32, and a cut surface position input means 33. Preferably, the 3D processor 23 is connected to an external storage or memory 34.

The 3D image generator 29 is provided with a coordinate conversion means for the picture signals of N-number of sequential unit picture images received from the two-dimensional ultrasound image processor 22, for generating signals of elemental picture images or elemental image segments to be patched into and displayed as an original 3D picture image. Further, by image processing operations at the 3D image processor 30, picture data of the respective elemental images from the 3D image generator 29 are pasted in predetermined positions on a 3D coordinate system, including image processing to erasing hidden surfaces from view. The resulting processed picture data are output to the image display device 6b through the display interface 31.

The 3D image view control 32 controls the 3D image generator 29 and the 3D image processor 30. The cut surface position input means 33 may be keyboard, mouse, touch pen or other input means which can input cut lines on an original 3D picture image on display on the monitor screen. The external storage 34 is a magnetic disc drive or any other storage means as long as it can store picture data of sequentially captured two-dimensional radial ultrasound picture images after coordinate conversion by the 3D image generator 29.

Figure 5:
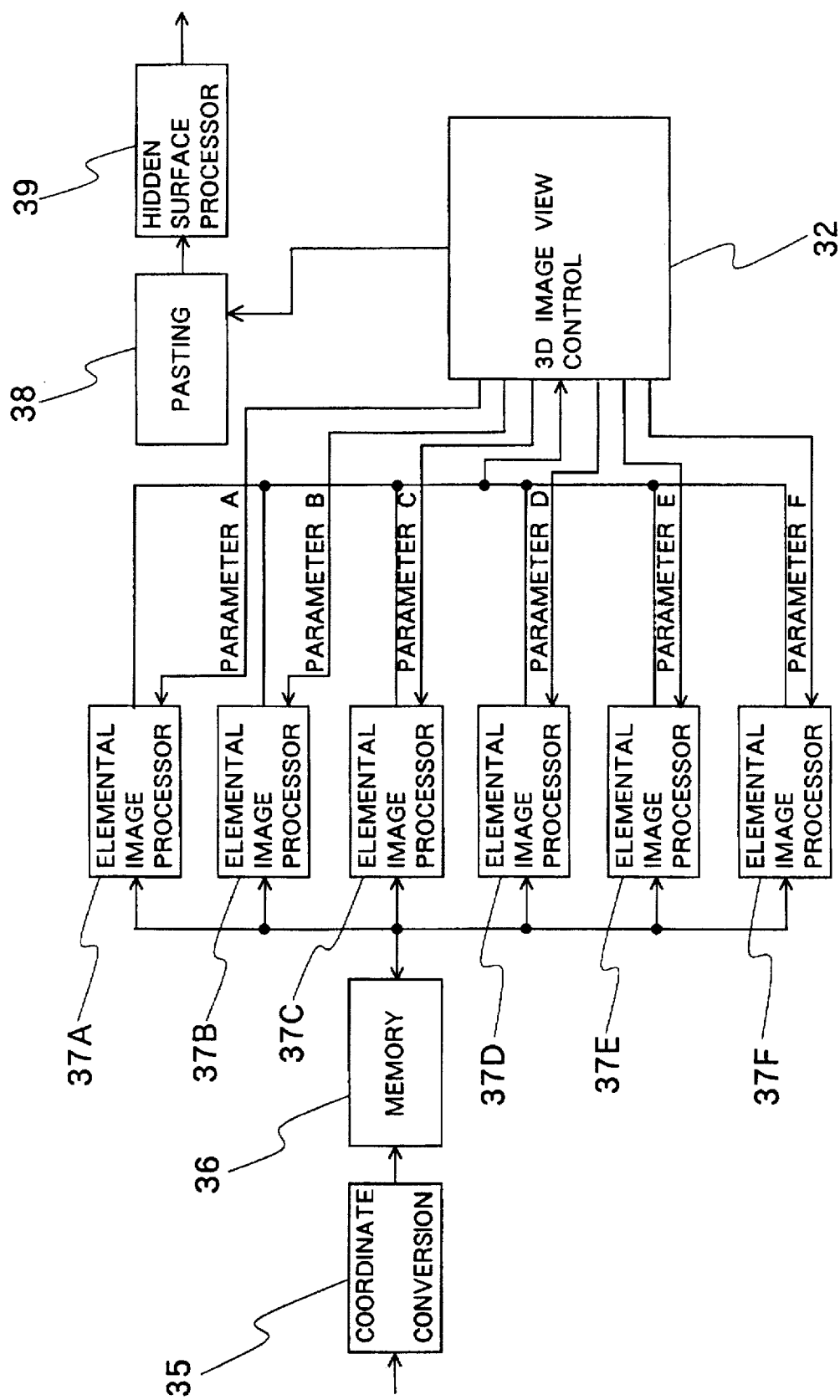
FIG. 5 is a block diagram of a 3D processor section of the signal processor of FIG. 4.

Shown in FIG. 5 are more specific forms of the above-described 3D image generator 29, 3D image processor 30 and 3D image view control 32. As seen in that figure, the 3D image generator 29 is provided with a coordinate conversion circuit 35, memory device 36 and a plural number of elemental image processing circuits 37A to 37F. In this instance, the number of the elemental image processing circuits depends on the number of elemental images which constitute an original 3D image to be displayed, and six elemental image processing circuits 37A to 37F are used in the particular example shown in FIG. 5. At the elemental image processing circuits 37A to 37F, the respective elemental picture images or segments, which constitute a 3D picture image, are processed from the coordinate-converted picture data of unit picture images. A 3D ultrasound picture image built up from the respective elemental images is displayed on the viewing screen 6b of the monitor basically in a regular perspective view either with or without an open cut-out section which exposes to view, for example, tissue structures interior of the original 3D image.

Figure 6:
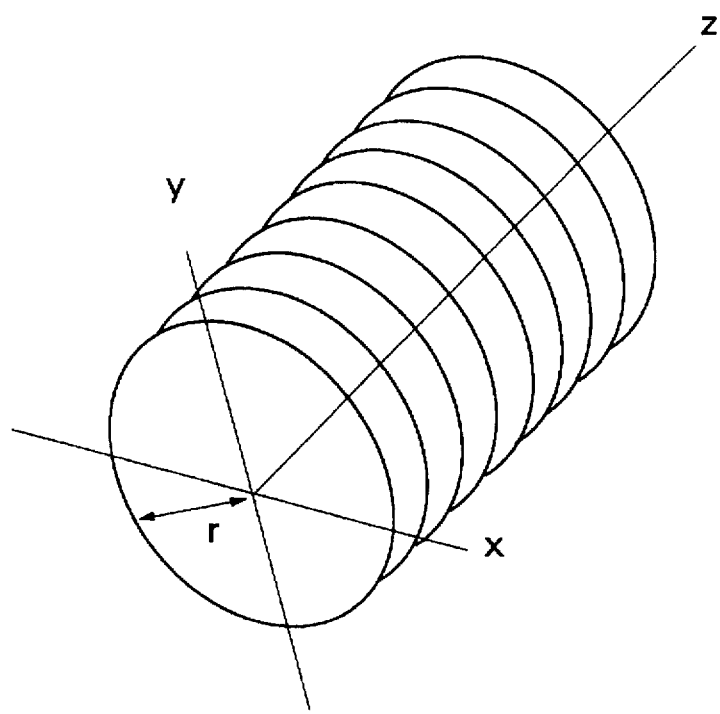
FIG. 6 is a diagrammatic illustration of series of sequentially captured two-dimensional ultrasound images lined up on a 3D coordinate system prior to building up an original 3D image.

When an original 3D ultrasound image is displayed on the monitor screen 6b as a perspective view taken from a predetermined direction, it shows the exterior surfaces of an image of aligned scanned sections or of the aligned unit picture images. More specifically, the unit picture images consisting of radial ultrasound picture images from the two-dimensional processor 22 are compiled into a 3D image of a columnar shape as a whole as shown in FIG. 6, on a 3D coordinate system having X-, Y- & Z-axes disposed at 60 degrees with each other to show the 3D image in a regular perspective view taken in the direction of the axis Z. In this instance, elemental picture images in the original 3D image are made up of a head-end elemental image segment A corresponding to the first unit picture image, an intermediate image segment B of a cylindrical shape connecting contours of the unit picture images of the 2nd to (N−1) positions, and a tail-end image segment C corresponding to the unit picture image in the last N-th position. In this regard, since the radial ultrasound images for the unit picture images 1 to N are captured by shifting the position of the ultrasound transducer 10 in a predetermined pitch in the axial direction, the 3D ultrasound picture image which is obtained by the above 3D processor looks extremely coarse if displayed as it is. Therefore, preferably picture data in the elemental picture section B are implemented into a multiplied density by linear interpolation filling in picture data between adjacent unit picture images, storing the resulting (N×a) picture data are in the storage memory 36. This data interpolation contributes to enhance the resolution of the 3D ultrasound image to a significant degree. Besides, although only part of the elemental image segment B is shown on the monitor screen 6b, it is desirable to process the entire surfaces of the cylindrical image rather than limiting elemental image processing to those surfaces on display on the monitor screen 6b, in order to permit image rotations about Z-axis as will be explained hereinlater.

Figure 7:
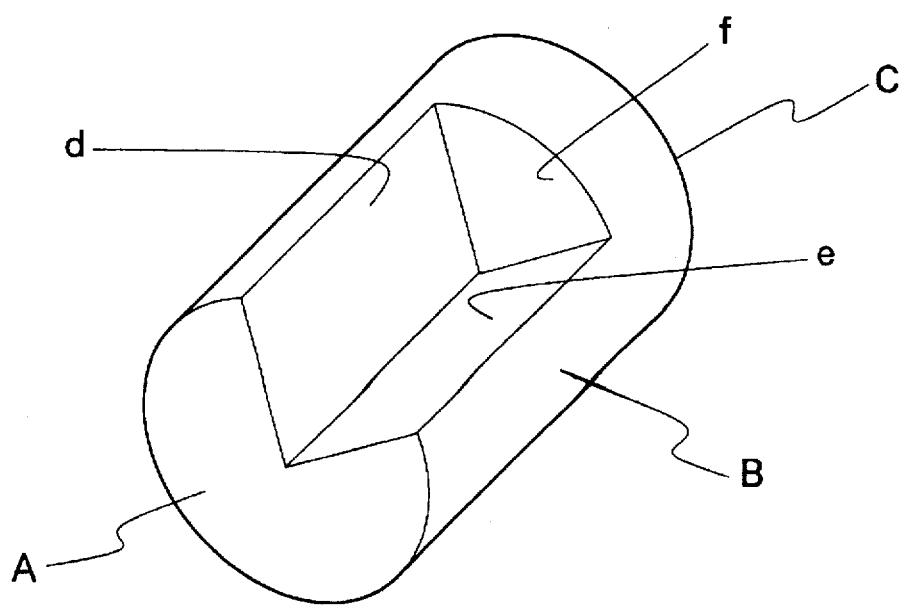
FIG. 7 is a diagrammatic illustration showing an example of a cut-out section opened in an original 3D ultrasound image.
Figure 8:
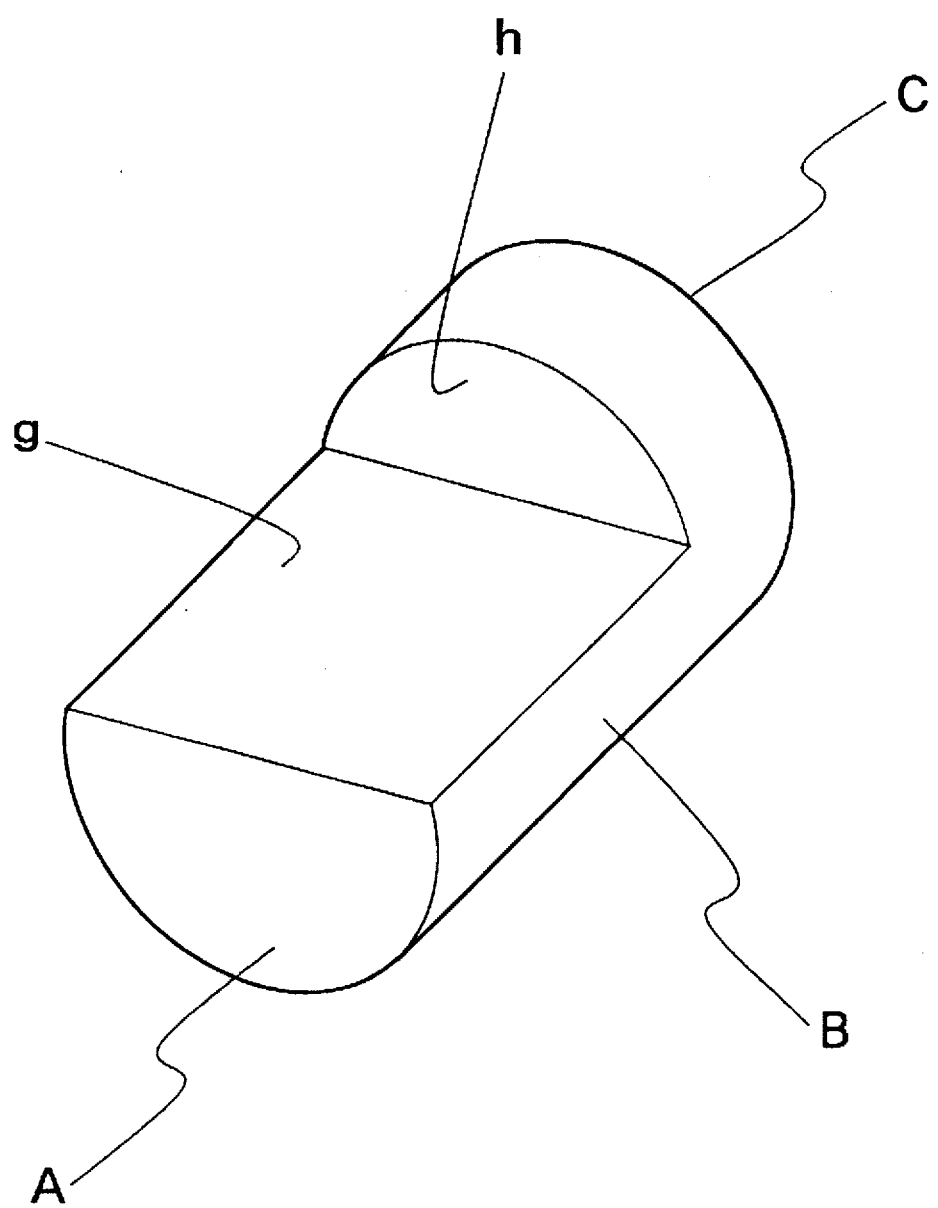
FIG. 8 is a view similar to FIG. 7, showing a different cut mode for the cut-out section.

Part of an original 3D picture image on display can be hollowed out by forming an open cut-out section which exposes to view interior structures of the image on and along cut surfaces of the open cut-out section. In forming an open cut-out section of this sort in an original 3D image, one can select a suitable cut mode, for example, a cut mode as shown in FIG. 7 or FIG. 8. More specifically, shown in FIG. 7 is a cut mode in which part of an original 3D image is hollowed out along two cut surfaces extending toward Z-axis and meeting with each other at a certain depth depending upon the cut angle. In the case of a cut mode as shown in FIG. 7, the open cut-out section contains cut surfaces "d" and "e", and, between these cut surfaces "d" and "e", a cut surface "f" which is a segment of a unit picture image of (N+1) position when the cut lines for the cut surfaces "d" and "e" extend up to a unit picture image of N-th position. Accordingly, in this case, the displayed 3D image with a cut-out section consists of six processed surface images, i.e., three elemental image segments A, B and C of the original 3D image plus elemental images of the three cut surfaces D, E and F. On the other hand, in a case where an original 3D image is horizontally cut out by a cut line extending up to a point short of the tail end of the cylindrical 3D image, say, extending up to a unit picture image in N-th position as shown in FIG. 8, the 3D image on display contains two cut surfaces, that is, a horizontal cut surface "d'" and a vertical cut surface "e'" which is a unit picture image in (N+1) position exposed as a result of the cut-out processing.

It follows that a 3D ultrasound image with a cut-out section is built up by pasting together a plural number of elemental images depending upon a selected cut mode. For this purpose, necessary elemental image segments are computed from picture data in N-number of unit picture images (actually from (N×a) unit picture images including interpolated picture data), and pasted on 3D coordinate axes. Pasting elemental image segments are processed according to parameters which are set up by the 3D image control view means 32 for the respective elemental image segments.

Of these elemental image segments of 3D image, certain elemental segments are invariable while certain elemental segments are variable depending upon a selected cut mode, namely, depending upon the positions and ranges of cut surfaces. Besides, when drawing the elemental image segments of 3D image on a two-dimensional plane, a certain elemental segment exactly corresponds to an original unit picture image while a elemental segment needs to be built up by gathering together a number of linear image segments in N-number of unit picture images over a certain surface area. In any case, it is necessary to determine which part of the unit picture images are to be used or processed in forming the respective elemental image segments of 3D image.

Then, based on definitive decisions on these points, the data of relevant elemental image segments of the 3D image are processed by the elemental image processing circuits 37A to 37F. In so doing, a plural number of elemental image segments can be processed either sequentially or parallelly. Any way, it is necessary to specify which elemental image segment is processed by which circuit. Further, it is necessary to determine the pasting positions of the processed elemental image segments on a 3D coordinate system. For this purpose, parameters are set for the respective elemental segments of 3D image, followed by execution of 3D image processing according to parameter settings.

Now, in case the original 3D image is of a columnar shape as shown in FIG. 6, it can be readily processed definitively as soon as 3D coordinate axe positions are set. In this case, the exterior surfaces of the 3D image are formed of three elemental image surfaces, i.e., the head- and tail-end surfaces and a cylindrical surface. Accordingly, parameters are set for the elemental images A, B and C which make up the 3D image surfaces.

On the other hand, in the case of a 3D ultrasound image with an open cut-out section, the image surfaces further include a number of cut surfaces depending upon the cut mode. Accordingly, parameters for the elemental images, which will make cut surfaces on the 3D image, change depending upon a selected cut mode. When a 3D image contains an open cut-out section with cut surfaces "d", "e" and "f" as shown in FIG. 7, these cut surfaces are added to the elemental image segments. For a cut-out section of the shape as shown in FIG. 8, cut surfaces "g" and "h" are added to the elemental image segments. In order to open a cut-out section as shown in FIG. 7, for example, parameters D to F are set for elemental image segments D to F which corresponds to the cut surfaces "d" to "f", respectively. In case two cut surfaces "g" and "h" are involved as in FIG. 8, different parameters G and H are set for the elemental image segments G and H, respectively. These parameters are allotted to the respective elemental image segments as soon as the corresponding cut mode is selected through the cut surface setting means 33. However, since each parameter contain variables, it becomes definitive only after the positions and ranges of the cut surfaces have been entered through the cut surface setting means 33. When previously specified position and range of a cut surface are changed, its parameter is changed accordingly.

Further, the 3D image processing circuit 30 executes necessary processing operations for building up a 3D ultrasound image with an open cut-out section on the basis of 3D image elemental segments generated by the 3D image generator 29. Accordingly, the 3D image processing circuit 30 includes a pasting image processor 38 for pasting the respective elemental image segments in predetermined positions on a predetermined 3D coordinate system, along with a hidden surface processor 39 for erasing picture data of surfaces to be hidden from view after the pasting operation.

Figure 9:
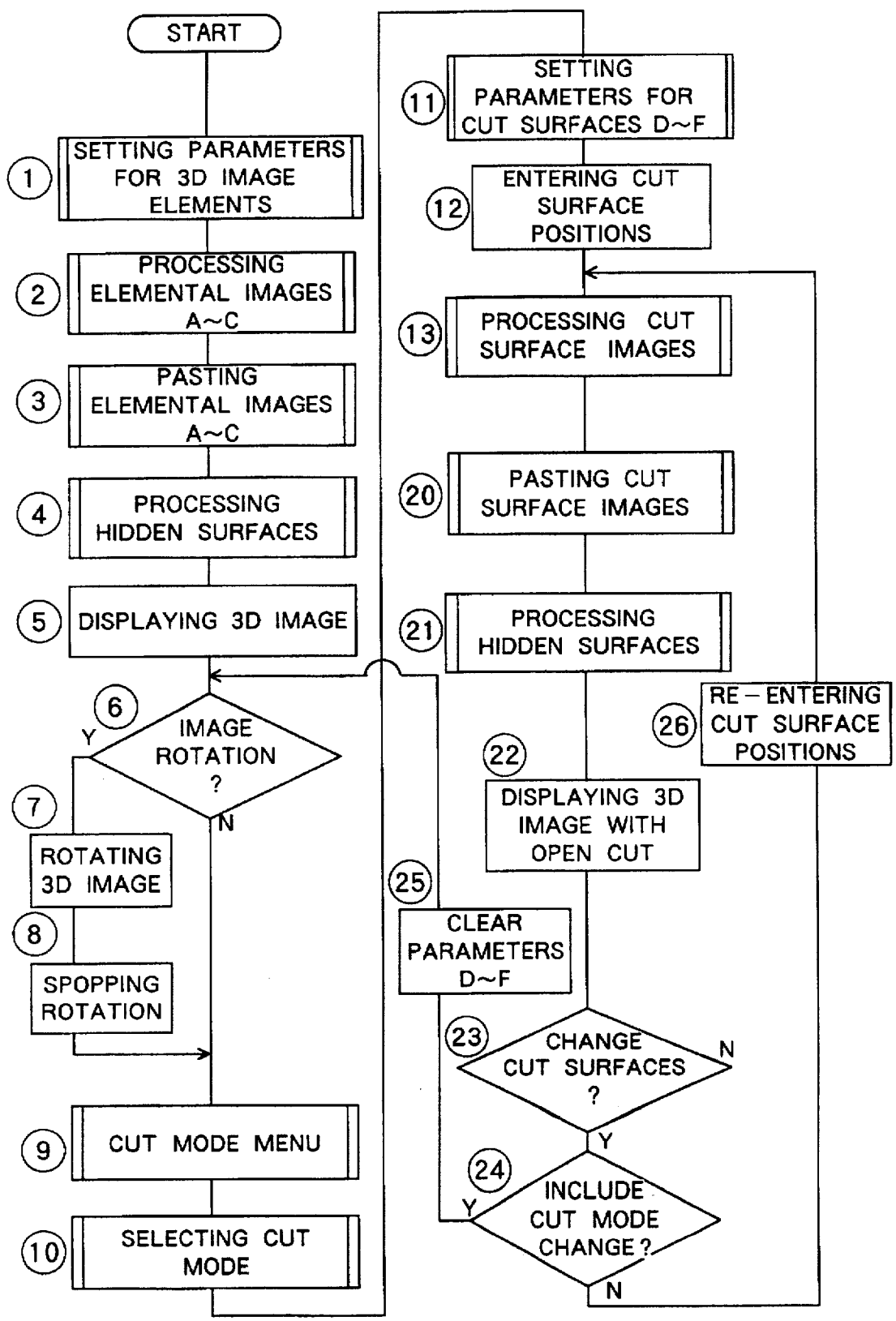
FIG. 9 is flow chart of a sequence for producing a 3D ultrasound image with an open cut-out section from a series of sequentially captured two-dimensional ultrasound images.
Figure 11:
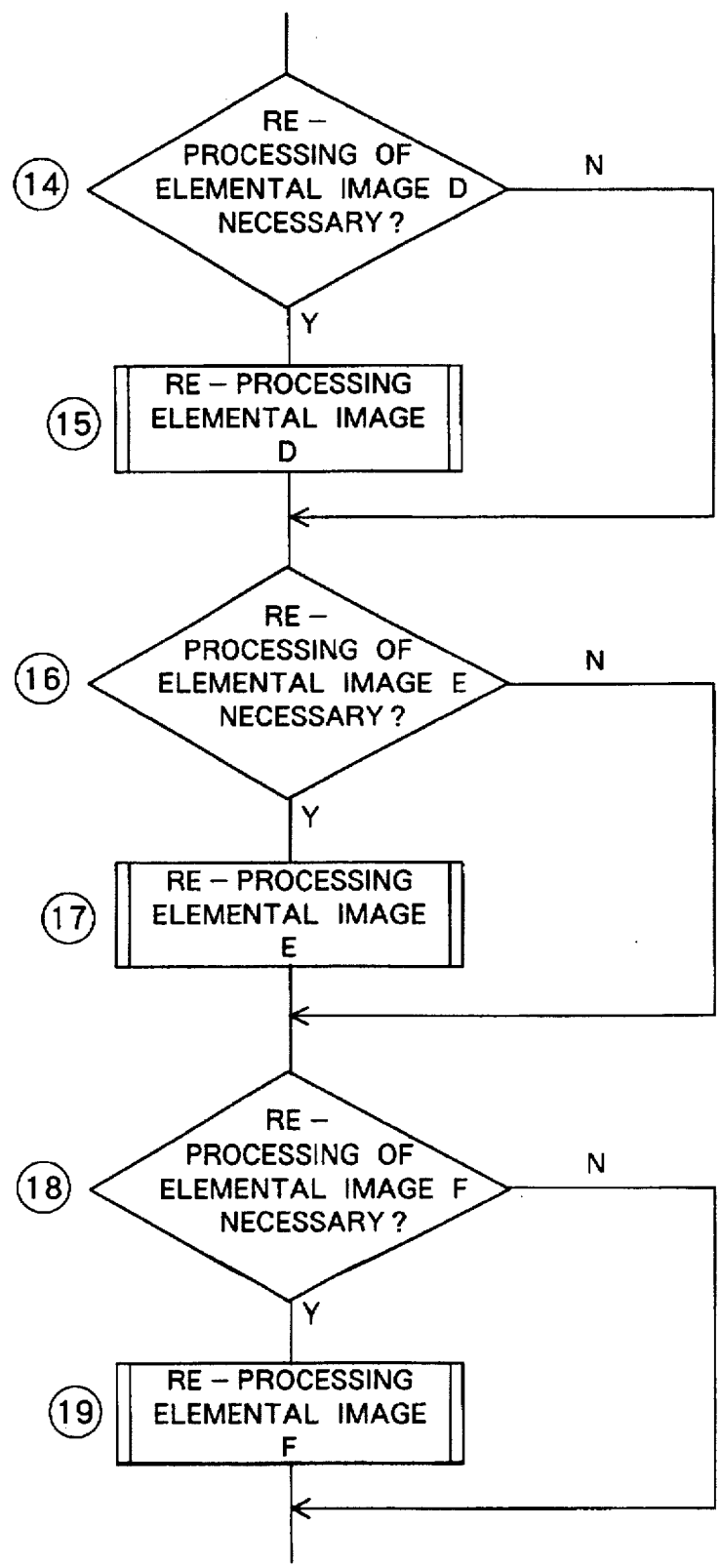
FIG. 11 is a flow chart of a subroutine for processing elemental images for altered cut surfaces.

Shown in FIG. 9 is a flow chart of the method of sequentially capturing 1st to N-th two-dimensional radial ultrasound images, which appear at the output of the two-dimensional ultrasound signal processor 22, into the 3D processor 23 as unit picture images and displaying a 3D ultrasound image on the monitor screen 6b.

The captured N-number of unit picture images are firstly fed to the coordinate conversion circuit 35 of the 3D image generator 29, and thereby converted into three-dimensionally correlated picture data, that is to say, N-number of unit picture images lined up on a 3D coordinate system, and implemented with picture data by linear interpolation between the respective two-dimensional radial ultrasound images. The resulting implemented picture data of N-number of unit picture images are stored in the external memory 36. Accordingly, it is to be understood that, in the following description, N-number of two-dimensional radial ultrasound images include the interpolated picture data even if not specifically mentioned. In this instance, the three axes X, Y and Z of the 3D coordinate system are set at an angle of 60 degrees with each other to show 3D ultrasound images on the monitor screen 6b in a regular perspective view taken from the direction of Z-axis. When the three axes are set in this manner, one can view and grip the structures of ultrasound images three-dimensionally on the monitor screen 6b from the most rational direction. However, the coordinate axes are not necessarily fixed in these positions and may be set in different positions or at different angles if desired.

Firstly, on the basis of the stored picture data, an original 3D image is produced and displayed on the monitor screen 6b of the ultrasound image observation terminal 6. The execution of 3D processing operations for an original 3D ultrasound image is started by pressing a corresponding key or keys or by clicking a corresponding command with a mouse. In this case, since the unit picture images are two-dimensional radial ultrasound images of a circular shape, the resulting original 3D image comes in a columnar shape as shown in FIG. 6. In this case, the original 3D picture image consists of three elemental segments, i.e., a first elemental image segment A consisting of the head unit picture image, a second elemental image segment B cylindrically connecting contours of unit picture images in the 2nd to (N−1)th positions, and a third elemental image segment C consisting of the last unit picture image in the N-th position. On X-, Y- and Z-axes of the 3D coordinate system, the original 3D image appears in a cylindrical shape having a radius "r" and extending from position "0" to position "N−1". Three parameters A to C are set for the three elemental image segments of the 3D image, i.e., a parameter A for the circular image surface of the radius "r" located at position "0" on axis Z, a parameter B for the cylindrical image surface of the radius "r" connecting circular contours of images in positions "1" to "N−1" on Z-axis, and a parameter C for the circular image surface of the radius "r" in position "N−1" on Z-axis. Then, elemental image processing circuits 37A to 37C are specified to generate the elemental images of parameters A to C for these 3D image surfaces. Accordingly, the elemental image processing circuits 37A to 37C are put in operation to generate an elemental image A corresponding to one unit picture image in the head-end position, an elemental image B of a cylindrical shape, and an elemental image C corresponding to one unit picture image in N-th position.

Image processing operations for these three elemental image segments A to C of the original 3D image are executed in Step 2 of the flow chart. In this case, however, for the elemental image segments A and C which exactly correspond to the first and last unit picture images, it suffices to read in the corresponding picture data from the memory 36. On the other hand, the elemental image segment B needs to be formed by processing picture data of the 2nd to (N−1)th unit picture images, more specifically, by reading in picture data of contours of the 2nd to (N−1)th unit picture images and aligning them cylindrically in the direction of Z-axis. As a result of these processing operations, each one of the elemental image segments A to C of the original 3D image is generated quite easily.

The picture data of the respective elemental image segments A to C are fed to the 3D image processor 30 to execute pasting operations for the image segments A to C at its pasting image processing circuit 38 (Step 3). The pasting is effected to the respective predetermined positions on the 3D coordinate axes, pasting the elemental image segment A at position "0" on Z-axis while pasting the elemental image segments B and C at positions "1" to "N−2" and at position "N−1" of Z-axis. Subsequent to the image pasting, image processing for hidden surfaces is executed at the hidden surface processing circuit 39 to erase the surfaces to be hidden from the view (Step 4). By these operations, an original 3D ultrasound image is generated and, through the display interface 31, displayed on the viewing screen 6b (Step 5).

In this state, part of the original 3D image is hollowed out by opening a cut-out section of an arbitrary shape in a particular region of interest. In this connection, there may arise a necessity for making a cut into a surface which is on the hidden side of the original 3D image currently on display on the viewing screen 6b. To comply with such a necessity, the original 3D image has to be rotated about Z-axis. In such a case, by way of an image rotation command menu which is indicated on the monitor screen, the operator can select either an "IMAGE ROTATION" or "NO IMAGE ROTATION" command (Step 6). Upon selecting an "IMAGE ROTATION" command, the original 3D image begins to rotate about Z-axis (Step 7), and stops its rotation as soon as a "STOP" command is entered (Step 8). Thus, the rotation of the original 3D image can be stopped when an image side of particular interest comes into view.

In case the image rotation is not necessary or when the original 3D image has been turned into a desired view position, a cut mode command menu is put on the viewing screen (Step 9), for example, for selecting a V-cut mode as shown in FIG. 7 or a mode of planar cut in the direction of Z-axis as shown in FIG. 8. Of course, the cut mode command menu may include other selectable cut modes, for instance, a cut along a plane perpendicular to Z-axis or an arcuate cut which exposes interior structures of the image on a curved surface instead of a planar or straight cut surface.

When a particular cut mode on the menu is selected (Step 10), the number of cut surfaces and the cut position are determined. More specifically, for example, when a V-cut mode of FIG. 7 is selected, the cut involves three cut surfaces "d", "e" and "f" and therefor three parameters D to F are set (Step 11) to generate three elemental image segments D to F. These parameters D to F are variable parameters which change depending upon the positions and ranges of cut surfaces, unlike the parameters A to C for the three elemental image segments A to C of the original 3D image. As shown in FIG. 10, the parameter D for the elemental image segment D defines a surface which is bounded by coordinates $(x_{n1}, y_{m1}, z_0)$, $(x_{n2}, Y_{m2}, z_0)$, $(x_{n1}, y_{m1}, z_{n-1})$ and $(x_{n2}, y_{m2}, z_{n-1})$, the parameter E for the elemental image segment E defines a surface which is bounded by coordinates $(x_{n1}, y_{m1}, z_0)$, $(x_{n3}, Y_m3, z_0)$, $(x_{n1}, y_{m1}, z_{n-1})$ and $(x_{n3}, y_{m3}, z_{n-1})$, and the parameter F for the elemental segment F defines a circle of a radius "r" at position "n" on Z-axis (where $x_{n1}+y_{m1}2<r_2$, $x_{n2}2+y_{m2}2=x_{n3}2+y_{m3}2=r_2$, $0<n<N-1$). The elemental image processing circuits 37D to 37F are designated to process the elemental image segments D to F according to parameters D to F, respectively.

In this manner, parameters are set for the elemental image segments of cut surfaces, thereby to specify the positions and ranges of the respective cut surfaces which are entered through the cut surface setting means 33 such as keyboard, mouse, touch pen or the like (Step 12). Cut surfaces are determined definitively by entering the coordinates $(x_{n1}, y_{m1}, z_0)$, $(x_{n2}, y_{m2}, z_0)$ and $(x_{n3}, y_{m3}, z_0)$ and the value of "n".

The determination of cut surfaces is followed by execution of a subroutine for processing the elemental image segments D to F (Step 13). This subroutine starts with a step (Step 14) to check whether or not image processing is necessary for the elemental image segment D, and, if necessary, the elemental image segment D is processed at the elemental image processing circuit 37D (Step 15). For processing the elemental image segment D, picture data on a line which connects the coordinates $(x_{n1}, y_{m1},)$ and $(x_{n2}, y_{m2},)$ are read out from the memory 36 successively from the 1st to N-th position in the direction of Z-axis. In this instance, a series of line segments which constitute the elemental image segment D are converted into surface data. The processing of the elemental image segment D is followed by a step (Step 16) to check if image processing is necessary for the elemental image segment E, and, if necessary, the elemental image segment E is processed at the elemental image processing circuit 37E, similarly reading out picture data on a line which connects coordinates $(x_{n1}, y_{m1},)$ and $(x_{n3}, y_{m3},)$ from the memory 36 successively from the 1st to N-th position in the direction of Z-axis (Step 17). This is followed by Step 18 to check if image processing is necessary for the elemental image segment F, and, if necessary, the elemental image segment F is processed at the elemental image processing circuit 37F. However, in this case the elemental image segment F is a two-dimensional radial ultrasound image in position "n" on Z-axis, so that it suffices to read out its picture data from the memory 36. Of course, instead of the above-described sequential operations, the elemental image segments D to F may be processed by parallel operations if desired.

As a result of execution of the subroutine for processing the elemental image segments D to F of the cut surfaces "d" to "f", all the elemental image segments D to F which are necessary for the cut surfaces of FIG. 10 are now obtained, in addition to the elemental image segments A to C of the original 3D ultrasound image.

According to the parameters E, E and F, these elemental image segments D, E and F are pasted in specified positions on the original 3D image (Step 20) which is on display on the viewing screen 6b, followed by a hidden surface processing in Step 21 to erase those surface portions to be hidden from view and displaying a 3D ultrasound image with an open cut-out section on the viewing screen (Step 22). Hidden surface portions of the respective elemental image segments are indicated by hatching in FIG. 10. With regard to the elemental image segment B, the hidden surface processing includes erasure of surfaces on the other side of the picture image away from the side which is seen in the drawing. The elemental image segment C is totally processed as a hidden surface except for its contour line.

In Step 23, the cut mode of the open cut-out section in the 3D ultrasound image on display can be altered if necessary. In altering the cut mode, changes can be made not only to the position and range of the cut-out section but also to the shapes and directions of cut surfaces. Accordingly, the nature of alteration is checked in Step 24, and, in the event of a change of cut mode, all of the parameters D to F of the current cut surfaces are cleared (Step 25) to show on the monitor screen 6b the original 3D ultrasound image in the same view as the one which was once displayed before the image rotation. The cut mode can be altered by changing one or more settings in the three coordinate positions $(x_{n1}, y_{m1}, z_0)$, $(x_{n2}, y_{m2}, z_0)$ and $(x_{n3}, y_{m3}, z_0)$ and the value of "n" (Step 26).

The changes to the cut surfaces are executed by a subroutine of Step 14 to Step 19. In this subroutine, a check is made in Steps 14, 16 and 18 as to whether or not the alteration necessitates re-processing of any elemental image segment. Therefore, upon changing a cut mode, image reprocessing is limited to an elemental image segment or segments of a cut surface or surfaces to be altered, excluding the elemental image segments of cut surfaces which will be unchanged. For example, in case a different setting is entered for the coordinate position $(x_{n2}, y_{m2}, z_0)$, this change does not necessitate to alter cut surfaces other than the cut surface "d" and therefore the elemental image segment D of the cut surface D alone is processed at the elemental image processing circuit 37D. The altered elemental image segment D is then pasted on the original 3D image, followed by a hidden surface processing in conformity with the altered elemental image segment D to show an open cut section of a different cut mode on the original 3D ultrasound image on display on the viewing screen 6b.

In displaying a 3D ultrasound image on a 3D coordinate system on the basis of a series of sequentially captured two-dimensional radial ultrasound images as described above, part of the 3D image is hollowed out at an open cut-out section exposing an interior region or regions of particular interest to direct view instead of been seen through the surfaces of the 3D image, and this is achieved by extremely simple signal processing operations, namely, simply by converting the sequentially captured two-dimensional radial ultrasound images into unit picture images lined up in three-dimensionally correlated positions, and cutting out and pasting picture data of 3D image surfaces including cut surfaces of the open cut-out section from picture data of the two-dimensional unit picture images stored in the memory 36. Therefore, it becomes possible to display 3D ultrasound images on a monitor screen quickly by the use of simple and inexpensive signal processing means. Besides, the 3D image on display contains an open-cut section which can expose to view, for example, internal tissue structures in a particular region of interest of the 3D image in various cut modes, permitting the observer to grip the information of such tissue structures three-dimensionally. As described above, alterations to cut surfaces can be completed easily and quickly by omitting image re-processing operations on elemental picture images other than altered cut surfaces.

Accordingly, for example, in case of an original 3D ultrasound image with an open V-cut having, as shown in FIG. 12, a couple of cut surfaces "d" and "e" intersecting with each other at a position of $x_{n1}=0$ and $y_{m1}=0$ and extending end to end throughout the length of the 3D image without forming a third cut surface "f", the viewer can grasp overall information on interior tissue structures of the 3D image by rotating the V-cut section in the direction of arrow S. In this state, should there arise a necessity for closer examinations on a particular region or spot P, the operator can easily grasp the shape of the spot P three-dimensionally by changing settings of the V-cut in such a way that the cut surfaces "d" and "e" are located immediately on the opposite sides of the spot P of particular interest and shifting another transverse cut surface "f" continuously or intermittently, for example, from the rear to front side of the spot P in the direction of arrow T.

What is claimed is:

1. A three-dimensional ultrasound image processing system, comprising:

a two-dimensional ultrasound image capture means for capturing a series of two-dimensional tomographic ultrasound images in sequentially shifted positions in a direction perpendicular to planes of said two-dimensional ultrasound images; and a 3D processor including a 3D image generator for compiling picture signals of said sequentially captured two-dimensional ultrasound images directly into picture data of a series of unit picture images lined up in three-dimensionally correlated positions, a 3D image processor for producing, on the basis of said unit picture images, an original 3D ultrasound image for display on a viewing screen in relation with a predetermined three-dimensional coordinate system, and a 3D image view processor for opening a cut-out section in part of said original 3D ultrasound image on display on said viewing screen to expose to view interior portions of said 3D ultrasound image on and along cut surfaces of said open cut-out section.

2. A three-dimensional ultrasound image processing system as defined in claim 1, wherein said two-dimensional ultrasound image capture means comprises a radial scan ultrasound transducer to be shifted in a direction perpendicular to planes of radial scan planes for capturing a series of a predetermined number of two-dimensional radial ultrasound images in a predetermined pitch in that direction.

3. A three-dimensional ultrasound image processing system as defined in claim 2, wherein said 3D image generator of said 3D processor is adapted to line up said sequentially captured radial ultrasound images along Z-axis of a three-dimensional coordinate system at the angle of 60 degrees with X- and Y-axes of the coordinate system, compiling the two-dimensional radial ultrasound images into an original 3D image in a regular perspective view.

4. A three-dimensional ultrasound image processing system as defined in claim 3, wherein said 3D processor comprises an image rotation processor for turning said original 3D image about said Z-axis.

5. A three-dimensional ultrasound image processing system as defined in claim 1, wherein said 3D processor includes cut surface processors to exhibit interior structures of said original 3D ultrasound image according to settings of an arbitrarily selected or altered cut mode.

6. A three-dimensional ultrasound image processing system as defined in claim 1, wherein said 3D processor comprises a coordinate conversion means for allocating said two-dimensional ultrasound images on a three-dimensional coordinate system through coordinate conversion, a cut surface position input means for entering cut mode and position for a cut-out section to be opened on said original 3D image, a 3D image control means for dissolving a 3D ultrasound image with an open cut-out section into a number of elemental images and setting parameters for the respective elemental images, an elemental image processing means for processing elemental images according to the respective parameters, and a 3D image view control means for pasting said elemental images in position on the three-dimensional coordinate system and erasing those surfaces hidden from view in a regular perspective view of said 3D ultrasound image with said open cut-out section, said 3D image processing means being arranged to re-process elemental images of altered cut surfaces alone when changing the cut mode of said open cut-out section.

* * * * *